(12) United States Patent
Ikeuchi

(10) Patent No.: US 10,157,260 B2
(45) Date of Patent: Dec. 18, 2018

(54) WALKING STATE ESTIMATING DEVICE AND WALKING STATE ESTIMATING METHOD

(71) Applicant: HONDA MOTOR CO., LTD., Tokyo (JP)

(72) Inventor: Yasushi Ikeuchi, Saitama (JP)

(73) Assignee: HONDA MOTOR CO., LTD., Tokyo (JP)

( * ) Notice: Subject to any disclaimer, the term of this patent is extended or adjusted under 35 U.S.C. 154(b) by 981 days.

(21) Appl. No.: 14/567,497

(22) Filed: Dec. 11, 2014

(65) Prior Publication Data
US 2016/0171171 A1    Jun. 16, 2016

(51) Int. Cl.
*G06F 7/60* (2006.01)
*G06F 17/10* (2006.01)
*G06F 19/00* (2018.01)
*G16H 50/50* (2018.01)

(52) U.S. Cl.
CPC .............. *G06F 19/00* (2013.01); *G16H 50/50* (2018.01)

(58) Field of Classification Search
CPC ........................................................ G06F 19/00
USPC ............................................................. 703/2
See application file for complete search history.

(56) References Cited

U.S. PATENT DOCUMENTS

| 6,243,623 B1 * | 6/2001 | Takenaka | B62D 57/02 180/8.1 |
| 2007/0267994 A1 * | 11/2007 | Sugihara | B62D 57/032 318/568.12 |
| 2009/0281462 A1 * | 11/2009 | Heliot | A61B 5/1038 600/595 |

FOREIGN PATENT DOCUMENTS

JP           5117123           10/2012

* cited by examiner

*Primary Examiner* — Timothy A Mudrick
(74) *Attorney, Agent, or Firm* — Rankin, Hill & Clark LLP

(57) ABSTRACT

Provided are a walking state estimating device and a walking state estimating method. A reference point Q (m) is defined at the bottom end portion of one of the pair of legs of a subject P, the one leg being estimated to be in a stance leg state, i.e. the one leg that is highly likely to be the supporting leg when the subject P changes the position and attitude of his/her torso. Hence, when the reference point Q (m) is changed, the position of the current reference point Q (m) can be estimated with high accuracy on the basis of the position of a previous reference point Q (m−1) before the change and according to the attitudes of the torso and the one leg at the time point at which the current reference point is defined after the change.

6 Claims, 6 Drawing Sheets

WALKING STATE ESTIMATING DEVICE AND WALKING STATE ESTIMATING METHOD

BACKGROUND OF THE INVENTION

1. Field of the Invention

The present invention relates to a technique for estimating the walking state of a subject having a plurality of legs.

2. Description of the Related Art

There has been proposed a technical method for estimating the walking time and the walking speed of feet and by extension the length of stride and travel distance of a subject on the basis of output signals of an acceleration sensor attached to a foot of a human being, who is the subject (refer to Japanese Patent No. 5117123).

The technique is, however, an estimation method based on the motion of feet and does not take the motional state of a lower limb into account, leading to a high possibility of deteriorated accuracy of the estimation of a walking state.

SUMMARY OF THE INVENTION

An object of the present invention is to provide a device and a method that permit improved accuracy of the estimation of the walking state of a subject, such as a human being.

A walking state estimating device in accordance with the present invention comprises: a first arithmetic processing element configured to estimate, on each of a pair of legs of a subject, a stance leg state in which a bottom end portion is in contact with a floor surface and a swing leg state in which the bottom end portion is off the floor surface, and to define, provided that one leg of the pair of legs has been estimated to be in the stance leg state, a reference point at the bottom end portion of the one leg; a second arithmetic processing element configured to measure the attitudes of a torso and the pair of legs of the subject; and a third arithmetic processing element configured to estimate, in the case where the first arithmetic processing element has defined a current reference point that is different from a previous reference point, the position of the current reference point on the basis of the position of the previous reference point and the attitudes of the torso and the pair of legs of the subject measured by the second arithmetic processing element at the time point of the definition of the current reference point, and to estimate the position of a specified point fixed to and defined at the torso on the basis of the position of the current reference point and the attitudes of the torso and one leg at which the current reference point has been defined, the attitudes having been measured by the second arithmetic processing element after the time point of the definition of the current reference point, wherein the first arithmetic processing element, the second arithmetic processing element, and the third arithmetic processing element are constituted of the same processor or separate processors.

The third arithmetic processing element is preferably configured to estimate, in the case where the first arithmetic processing element has estimated that both of the pair of legs are in the stance leg state, the difference in height between the bottom end portions of the pair of legs on the basis of the attitudes of the torso and the pair of legs of the subject measured by the second arithmetic processing element so as to estimate the shape of the floor surface on the basis of the difference in height or to correct the position of the current reference point on the basis of the difference in height.

The third arithmetic processing element is preferably configured to determine whether the difference in height is a threshold value or less and outputs an estimation result indicating that the floor surface is a level surface in the case where a result of the determination is affirmative.

The third arithmetic processing element is preferably configured to determine whether the difference in height is the threshold value or less by using the threshold value set on the basis of an occurrence frequency distribution of the difference in height obtained from the results of a plurality of times of estimations of the difference in height or by using the threshold value set beforehand on the basis of an error of measurement by the second arithmetic processing element.

The first arithmetic processing element is preferably configured to estimate that the other leg is in the stance leg state in the case where it is estimated that one leg of the pair of legs in which the previous reference point has been defined at the bottom end portion thereof has been changed from the stance leg state to the swing leg state.

DESCRIPTION OF THE PREFERRED EMBODIMENTS (Constitution)

Figure 1:
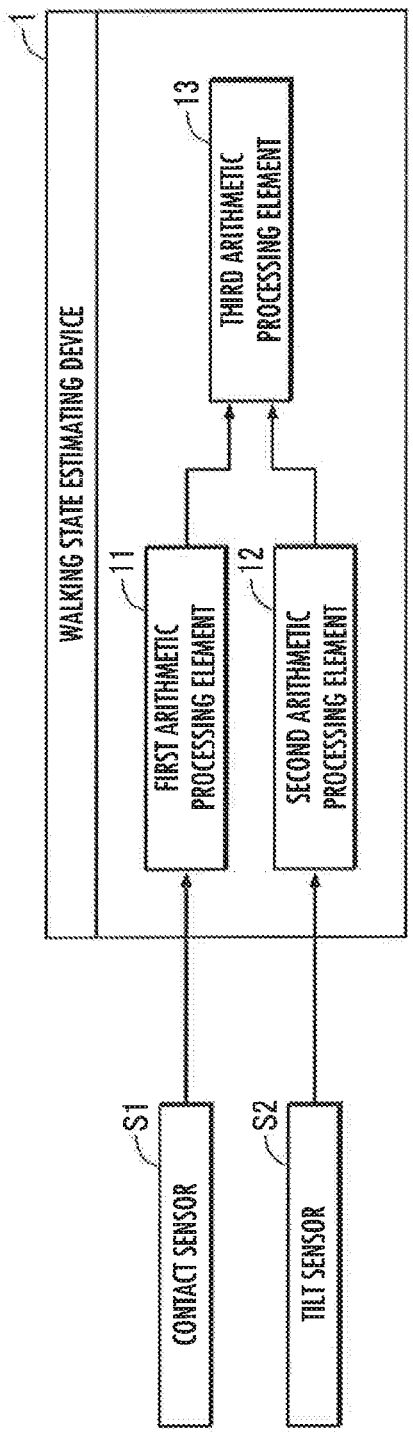
FIG. 1 is a block diagram of a walking state estimating device according to an embodiment of the present invention.

A walking state estimating device 1 as an embodiment of the present invention illustrated in FIG. 1 is adapted to estimate the walking state of a human being who is a subject. The walking state estimating method in accordance with the present invention can be applied to every agent capable of causing a pair of legs to land on a floor and leave from the floor thereby to move, as in the case where one or both of the left and right legs of a human being, who is a subject, are artificial limbs or in the case where the subject is a bipedal walking robot. Reference characters "L" and "R" will be used to distinguish the left and right of legs and the like, but the reference characters will be omitted in the case where there is no need to distinguish the left and right or in the case where vectors having left and right components are expressed.

The walking state estimating device 1 includes a first arithmetic processing element 11, a second arithmetic processing element 12, and a third arithmetic processing element 13, which are constituted of computers and adapted to carry out assigned arithmetic processing. The first arithmetic processing element 11 receives output signals from a contact sensor S1. The second arithmetic processing element 12 receives output signals from a tilt sensor S2. The contact sensor S1 may be a constituent of the first arithmetic processing element 11. The tilt sensor S2 may be a constituent of the second arithmetic processing element 12.

Figure 2:
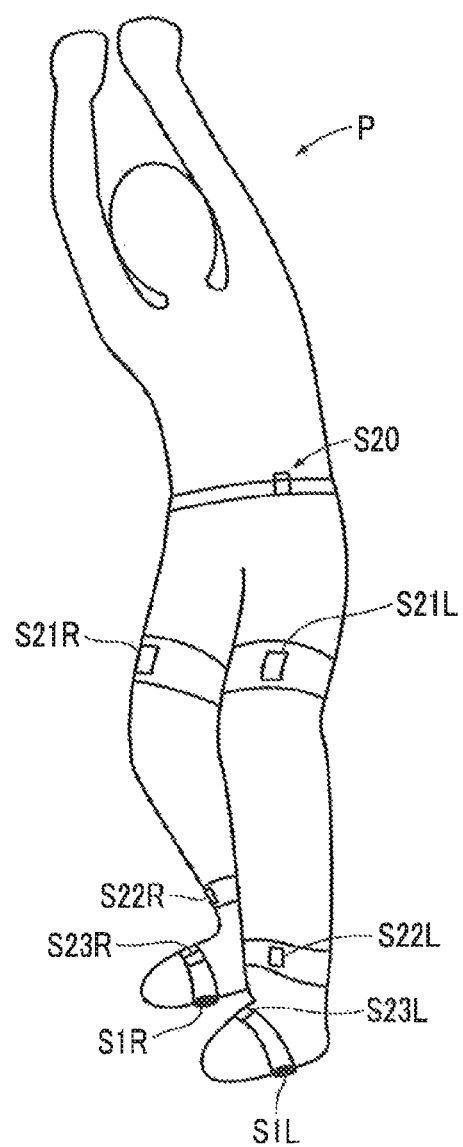
FIG. 2 is an explanatory diagram illustrating the placement of sensors.

The contact sensor S1 is constituted of a pair of left and right contact sensors S1L and S1R illustrated in FIG. 2. Each of the pair of contact sensors S1L and S1R is configured to output a signal based on the contact or no contact between an MP joint portion of each of the left and right feet of a subject P and a floor surface or based on the magnitude of a floor reaction force acting on each of the feet. The contact sensor S1 is disposed on the bottom or an insole of a shoe attached to a foot of the subject P.

The tilt sensor S2 is composed of a torso tilt sensor S20, a pair of left and right thigh tilt sensors S21L and S21R, a pair of left and right crus tilt sensors S22L and S22R, and a pair of left and right foot tilt sensors S23L and S23R illustrated in FIG. 2. Each of the torso tilt sensor S20, the thigh tilt sensors S21, the crus tilt sensors S22, and the foot tilt sensors S23 is configured to output signals based on rotational angles about three axes of the torso, the thigh, the crus, and the foot, respectively, of the subject P. Each of the torso tilt sensor S20, the thigh tilt sensors S21, the crus tilt sensors S22, and the foot tilt sensors S23 is fixed to a band attached to each of the torso, the thighs, the cruses, and feet of the subject P.

Configuring the arithmetic processing elements 11 to 13 so as to carry out the assigned arithmetic processing means that arithmetic processing units (CPUs) constituting the computers are programmed or designed to read necessary data and application software from a storage unit (memory) and carry out the predetermined arithmetic processing according to the software. The first arithmetic processing element 11, the second arithmetic processing element 12, and the third arithmetic processing element 13 may be constituted of the same hardware (a processor or a CPU and a memory and the like) or separate independent hardware (a processor or a CPU and a memory and the like) which is capable of communicating with each other.

(Function)

Regarding the functions of the walking state estimating device 1 having the foregoing configuration, the walking state estimating method according to an embodiment of the present invention will be described.

Figure 3:
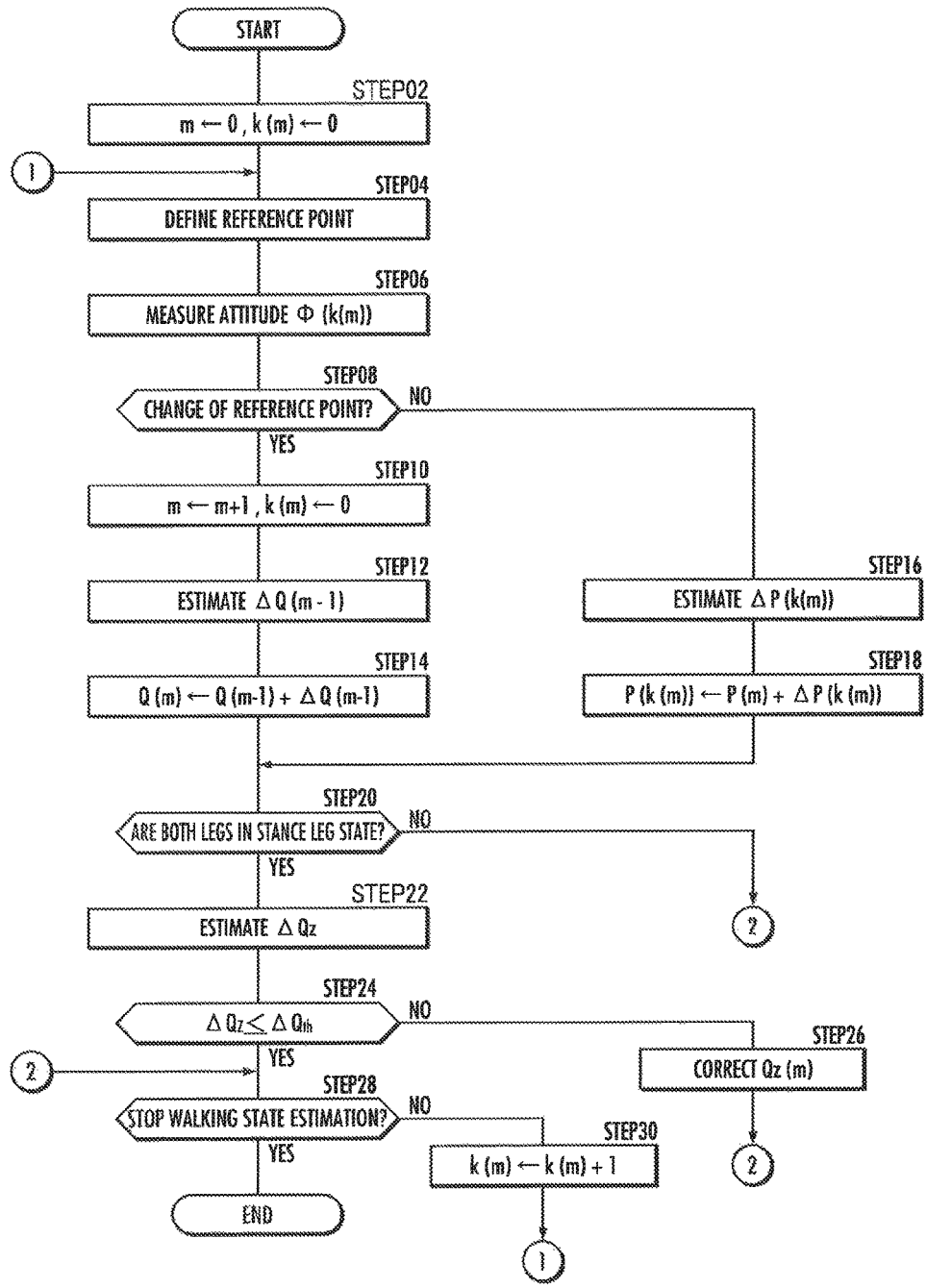
FIG. 3 is a flowchart illustrating a walking state estimating method according to an embodiment of the present invention.

First, an index "m" denoting the number of changes of a reference point and an index "k(m)" denoting the number of repetitions of an arithmetic processing cycle after a time point at which a latest reference point is defined and by extension the elapsed time are both reset to zero (STEP02 of FIG. 3).

A reference point is defined by the first arithmetic processing element 11 on the basis of an output signal from the contact sensor S1 (STEP04 of FIG. 3). Specifically, the reference point is defined at the MP joint portion of either the left foot or the right foot according to the rule illustrated in Table 1.

TABLE 1

| Location where reference point is defined | | Definition conditions |
|---|---|---|
| Right foot MP joint | 1 | The output signal of the right contact sensor S1R is ON, while the output signal of the left contact sensor S1L is OFF. |
| | 2 | In a state wherein the reference point has been defined at the left foot, the output signal of the left contact sensor S1L switches from ON to OFF. |
| | 3 | In a state wherein the reference point has been defined at the right foot, the output signal of the left contact sensor S1L switches from OFF to ON. |
| Left foot MP joint | 4 | The output signal of the left contact sensor S1L is ON, while the output signal of the right contact sensor S1R is OFF. |
| | 5 | In a state wherein the reference point has been defined at the right foot, the output signal of the right contact sensor S1R switches from ON to OFF. |
| | 6 | In a state wherein the reference point has been defined at the left foot, the output signal of the right contact sensor S1R switches from OFF to ON. |
| | 7 | The output signals of both the contact sensors S1R and S1L are ON in an initial state. |

In a period of time from the instant the floor reaction force indicated by an output signal of the contact sensor S1 reaches a first threshold value or more to the instant the floor reaction force reduces to equal to or less than a second threshold value, which is smaller than the first threshold value, the signal is defined as "ON," while the signal is defined as OFF in other cases. If the definition condition 3 in Table 1 is satisfied, then the reference point may be defined at the left foot MP joint rather than the right foot MP joint. If the definition condition 6 is satisfied, then the reference point may be defined at the right foot MP joint rather than the left foot MP joint. If the definition condition 7 is satisfied, then the reference point may be defined at the right foot MP joint rather than the left foot MP joint.

Figure 4:
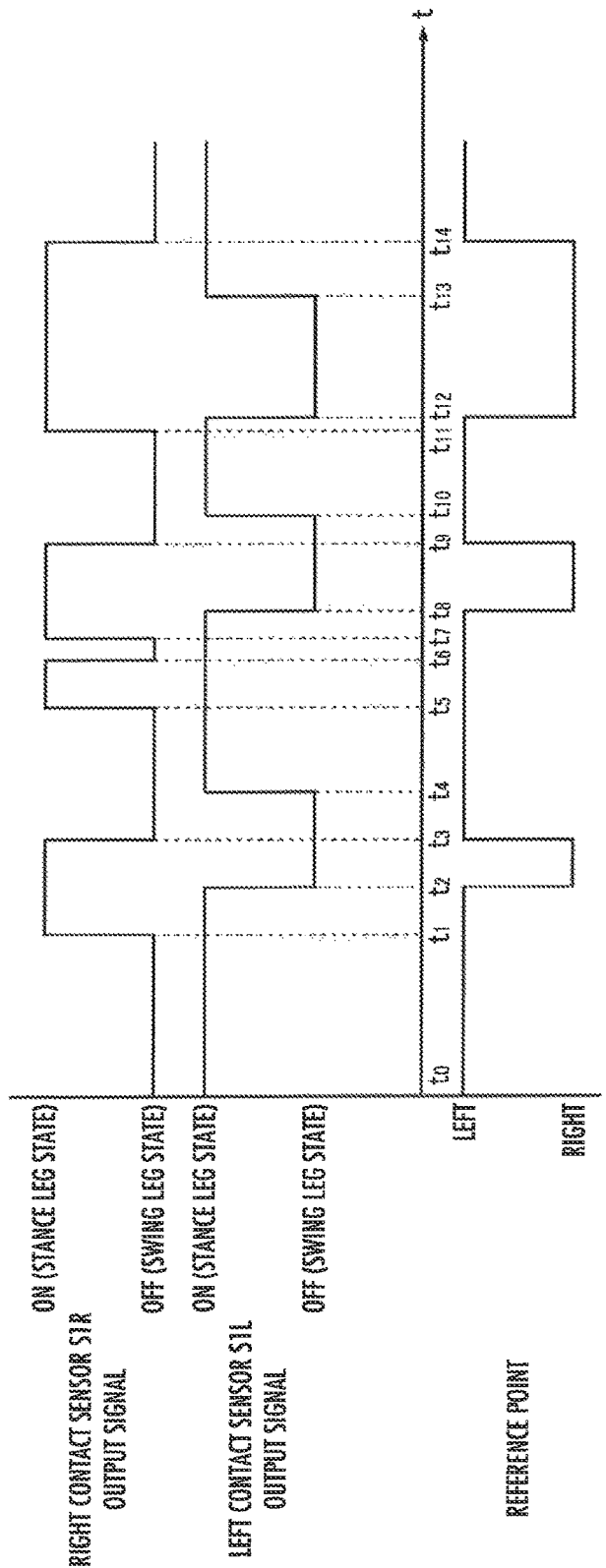
FIG. 4 is an explanatory diagram related to the definitions of reference points.

According to the rule given in Table 1, if the output signals of the contact sensors S1R and S1L change with time as illustrated on the upper side of FIG. 4, then the reference point is dynamically defined as illustrated on the lower side of FIG. 4. Table 2 illustrates all the output signals of the contact sensors S1R and S1L, respectively, at time t0 to t14 illustrated in FIG. 4, the change in the definition of the reference point, and the rules applied to the definition.

TABLE 2

| | Output Signal of Contact Sensor (○: ON/●: OFF/→: change to) | | Definition of Reference Point | Rule Applied in |
|---|---|---|---|---|
| Time | Right | Left | (→: change to) | Definition |
| t0 | ● | ○ | Left | 4 |
| t1 | ●→○ | ○ | Left | 6 |
| t2 | ○ | ○→● | Left → Right | 2 |
| t3 | ○→● | ● | Right → Left | 5 |
| t4 | ● | ●→○ | Left | 4 |
| t5 | ●→○ | ○ | Left | 6 |
| t6 | ○→● | ○ | Left | 4 |
| t7 | ●→○ | ○ | Left | 6 |
| t8 | ○ | ○→● | Left → Right | 2 |
| t9 | ○→● | ● | Right → Left | 5 |
| t10 | ● | ●→○ | Left | 4 |
| t11 | ●→○ | ○ | Left | 6 |
| t12 | ○ | ○→● | Left → Right | 2 |
| t13 | ○ | ●→○ | Right | 3 |
| t14 | ○→● | ○ | Right → Left | 5 |

According to the example in FIG. 4, the output signals of both the contact sensors S1R and S1L are OFF at the time periods of t3 to t4 and t9 to t10. This does not mean that both legs of the subject P are not in an in-the-air period, in which both legs of the subject P are in the swing leg state, but the output signals mean that the sensitivities of the contact sensors S1R and S1L have deteriorated due to, for example, improper installation thereof to the feet, whereas at least one of the legs is actually in the stance leg state.

The second arithmetic processing element 12 measures attitudes Φ (k(m)) of the torso and both legs of the subject P (STEP06 of FIG. 3) on the basis of an output signal of the tilt sensor S2. The attitude Φ (k(m)) is defined as a vector, the components of which are the rotational angles about three axes (the amount of angle change from an initial value) of each of the waist, thighs, cruses, and feet of the subject P at time t=k (m) (refer to FIG. 2).

The third arithmetic processing element 13 carries out the assigned arithmetic processing on the basis of the output results of the first arithmetic processing element 11 and the second arithmetic processing element 12. Specifically, first, it is determined whether a reference point defined by the first arithmetic processing element 11 has been changed (STEP08 of FIG. 3). For example, the determination result is affirmative at time t2, t3, t8, t9, t12, and t14 illustrated in FIG. 4, while the determination results are negative at the remaining times (refer to Table 2).

If the determination result is affirmative (YES in STEP08 of FIG. 3), then the value of the index m is incremented by 1, and the index k (m) is reset to zero (STEP10 of FIG. 3). Based on the attitudes Φ (k(m)) of the torso and the both legs of the subject P measured by the second arithmetic processing element 12, the previous reference point displacement vector ΔQ (m−1) is calculated according to a body model of the subject P (STEP12 of FIG. 3).

Figure 5:
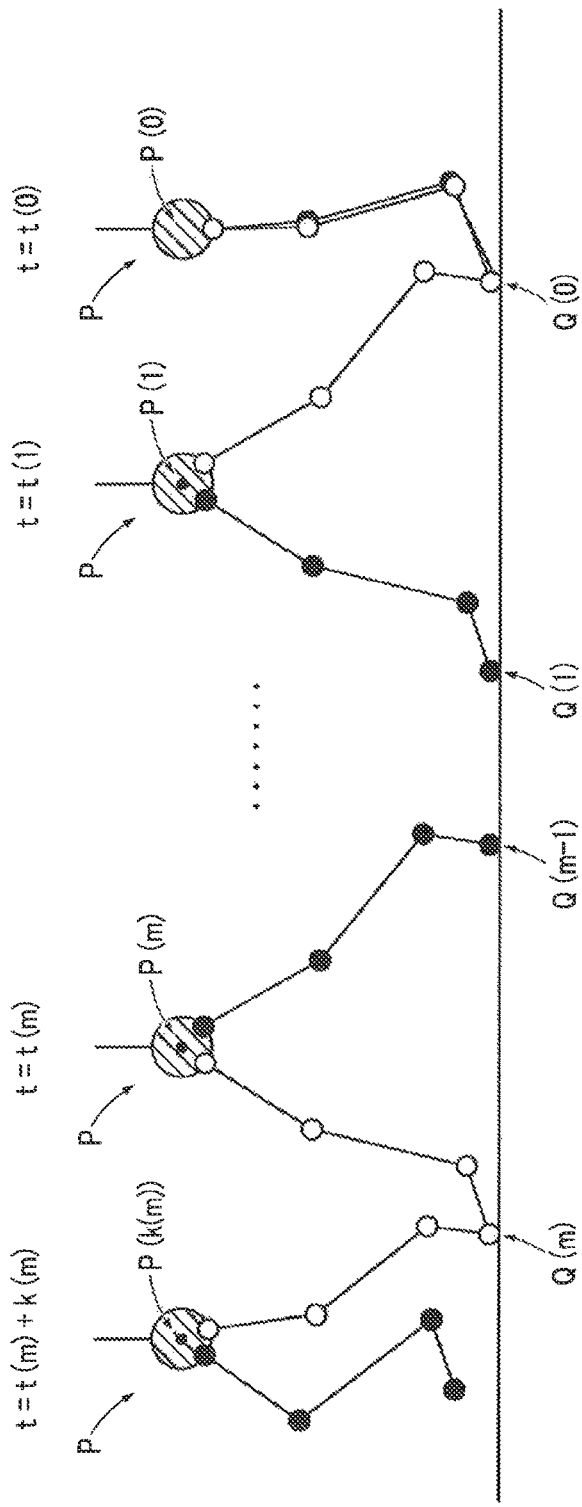
FIG. 5 is a conceptual explanatory diagram related to the walking state estimating method.

The previous reference point displacement vector ΔQ (m−1) is a vector, the start point of which is the previous reference point Q (m−1) and the end point of which is a current reference point Q (m) (refer to FIG. 5). The previous reference point and the current reference point are defined by the change of the value (+1) of the index m.

FIG. 5 illustrates the body model of the subject P. In FIG. 5, the waist of the subject P is denoted by a hatched circle; the hip joint, the knee joint, the foot joint and the MP joint of the right leg are denoted by black dots (●); and the hip joint, the knee joint, the foot joint and the MP joint of the left leg are denoted by blank dots (○). According to the body model, the origin of a body coordinate system in which the position and the attitude are fixed relative to the torso is defined as a specified point.

The position of each hip joint is defined by a coordinate value in the body coordinate system. The body model is defined by the length of the thigh (the interval between the hip joint and the knee joint), the length of the crus (the interval between the knee joint and the foot joint), and the length of the foot (the interval between the foot joint and the foot MP joint). The values of the parameters that define the body model are stored beforehand in a storage unit constituting the walking state estimating device 1 or in a storage unit constituting an external device capable of communicating with the walking state estimating device 1.

The values of the parameters may be manually or automatically set for each subject P, taking the difference in body type of the subject P into consideration. The values of the parameters may be laterally symmetrical or asymmetrical. This is implemented typically by a method in which an ID assigned to the subject P and parameter values, which are associated with the ID, are stored beforehand in a storage unit, and the values corresponding to the ID input through an appropriate interface are retrieved from the storage unit.

The case illustrated in FIG. 5 will be discussed. The reference point Q (0) is defined at the MP joint of the left foot in the initial state t=t (0), and the defined reference point is changed to a reference point Q (1), i.e. from the MP joint of the left foot to the MP joint of the right foot at time t=t (1). For simplicity, a level surface is used as a floor surface.

In this case, based on the initial attitude Φ (0) at time t=t (0) (the components denoting the attitudes of the torso, the left thigh, the left crus, and the left foot), the coordinate value of the initial reference point Q (0) in an initial body coordinate system is calculated according to the body model (at least the coordinate value of the left hip joint in the body coordinate system, the length of the left thigh, the length of the left crus, and the length of the left foot). In other words, a vector having a first specified point P (0) as the start point thereof and the initial reference point Q (0) as the end point thereof is calculated.

Further, based on the attitude Φ (1) at time t=t (1), a previous reference point displacement vector ΔQ (0) having the previous reference point (the first reference point) Q (0) as the start point thereof and the current reference point Q (1) as the end point thereof is calculated according to the body model.

Similarly, the previous reference point displacement vector ΔQ (m−1) is calculated also in the case where the reference point Q (m−1) is defined at the MP joint of the right foot at time t=t (m−1) in FIG. 5, and then the reference point Q (m) defined is changed from the MP joint of the right foot to the MP joint of the left foot at time t=t (m). The previous reference point displacement vector ΔQ (m−1) is defined in the initial body coordinate system at time t=t (0), but can be defined also in a world coordinate system if the relative position (denoted by a translation vector) of the initial body coordinate system with respect to the world coordinate system and attitude (denoted by rotation matrix or Euler angle or quarternion equivalent thereto) are known.

Then, as the result of a previous reference point position Q (m−1) having been translated by the previous reference point displacement vector ΔQ (m−1), a current reference point position Q (m) is calculated as the vector or the coordinate value in the world coordinate system or the initial body coordinate system (STEP14 of FIG. 3).

Meanwhile, if the determination result is negative (NO in STEP08 of FIG. 3), then a specified point displacement vector ΔP (k (m)) is calculated according to the body model of the subject P on the basis of the attitude Φ (m−1) and Φ (k (m)) of the torso and the both legs of the subject P measured by the second arithmetic processing element 12 (STEP16 of FIG. 3).

The specified point displacement vector ΔP (k (m)) is a vector, the start point of which is a specified point P (m−1) at the time point at which the previous reference point Q (m−1) was defined, and the end point of which is a current specified point P (k (m)) (refer to FIG. 5). Unlike the reference point, a previous specified point and a current specified point are defined by the change of the value (+1) of the index k (m) rather than the index m. In other words, a previous specified point P (k (m)−1) is defined with respect to the current specified point P (k (m)). If the current reference point Q (m) is defined after the specified point displacement vector ΔP (k (m−1)) is calculated for Nm−1 number of times for each control cycle Δt after the time point t (m−1) at which the previous reference point Q (m−1) was defined, then the time point t (m) at which the current reference point Q (m) is defined is denoted by t (m−1)+ Nm·Δt.

In the process of calculating the previous reference point displacement vector ΔQ (m−1) as described above, a vector, the start point of which is the specified point P (m−1) at the time point at which the previous reference point Q (m−1) was defined and the end point of which is the current reference point Q (m), can be also calculated. Based on a current measured attitude Φ (k (m)), a vector having the current reference point Q (m) as the start point thereof and the current specified point P (k (m)) as the end point thereof is calculated according to the body model. Both the vectors are added to calculate a specified point displacement vector ΔP (k (m)) (refer to FIG. 5).

Then, as the result that a specified point P (m−1) at the time point at which the previous reference point Q (m−1) was defined has been translated by the specified point displacement vector ΔP (k (m)), a current specified point position P (k (m)) is calculated as a vector or a coordinate value in the world coordinate system or the initial body coordinate system (STEP18 of FIG. 3).

Further, depending on whether the output signals of both the contact sensors S1R and S1L are ON, the first arithmetic processing element 11 determines whether both legs of the subject P are in the stance leg state (STEP20 of FIG. 3). According to the example illustrated in FIG. 4, the determination results are affirmative at time periods of t1 to t2, t5 to t6, t7 to t8, t11 to t12, and t13 to t14, while the determination results are negative in the remaining time periods (refer to Table 2).

If the determination result is negative (NO in STEP20 of FIG. 3), then it is further determined whether a stop condition, such as the lapse of predetermined time since the estimation of the walking state was started, is satisfied (STEP28 of FIG. 3).

Figure 6:
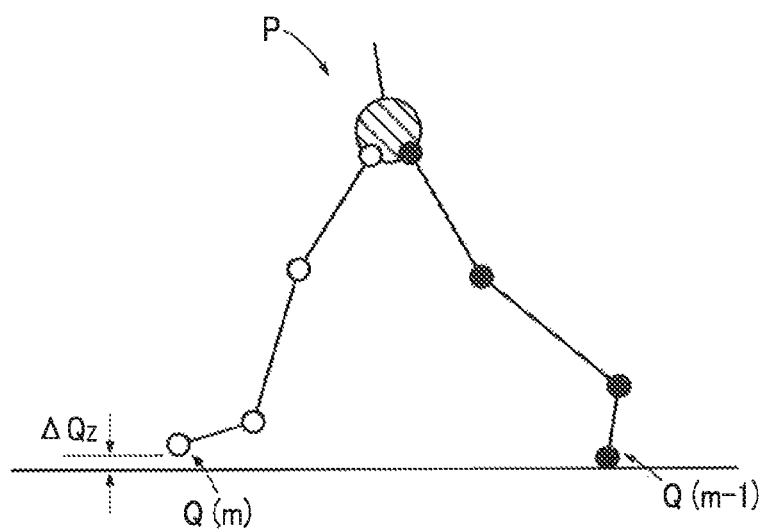
FIG. 6 is a conceptual explanatory diagram related to a method for correcting an estimated result of a walking state.

Meanwhile, if the determination result is affirmative (YES in STEP20 of FIG. 3), then a reference point height difference ΔQz in the world coordinate system is estimated (STEP22 of FIG. 3). The reference point height difference ΔQz is defined as the deviation of a z component Qz (m) of the current reference point Q (m) from the z component (component in a vertical direction) Qz (m−1) of the previous reference point Q (m−1), as illustrated in FIG. 6. It is determined whether the reference point height difference ΔQz is a threshold value ΔQth or less (STEP24 of FIG. 3).

As an alternative, the reference point height difference ΔQz may be estimated a plurality of times by the third arithmetic processing element 13 when the subject walks on the same floor surface beforehand and a predetermined value (e.g. a value that is two to three times a standard deviation σ) may be set as the threshold value ΔQth from a representative value indicating a maximum frequency on the basis of the occurrence frequency distribution of the reference point height difference ΔQz. Further alternatively, a threshold value ΔQth, which is set in advance on the basis of an error of measurement by the tilt sensor S2, may be used.

If the determination result is affirmative (YES in STEP24 of FIG. 3), then it is further determined whether the stop condition is satisfied (STEP28 of FIG. 3). In view of the determination results, the floor surface may be estimated as a level surface by the third arithmetic processing element 13 and the estimation result may be output.

Meanwhile, if the determination result is negative (NO in STEP24 of FIG. 3), then the z component Qz (m) of the current reference point Q (m) is corrected (STEP26 of FIG. 3), and it is further determined whether the stop condition is satisfied (STEP28 of FIG. 3).

For example, the z component Qz (m) of the current reference point Q (m) is corrected to zero. Alternatively, the z component Qz (m) of the current reference point Q (m) may be corrected by increasing or decreasing by an amount obtained by multiplying the reference point height difference ΔQz (m−1) by an appropriate gain coefficient G. Based on a determination result indicating that the reference point height difference ΔQz exceeds the threshold value ΔQth, it may be estimated by the third arithmetic processing element 13 that a floor surface has a step or a tilt corresponding to the threshold value ΔQth.

If it is determined that the walking state estimation stop condition is not satisfied (NO in STEP28 of FIG. 3), then the index k (m) is incremented by 1 (STEP30 of FIG. 3) and the processing after the definition of the reference point (STEP04 of FIG. 3) is repeated. If it is determined that the walking state estimation stop condition is satisfied (YES in STEP28 of FIG. 3), then the series of the processing steps for estimating the walking state is terminated.

Advantages

According to the walking state estimating device 1, which exhibits the functions described above, the reference point Q (m) is defined at the bottom end portion of one leg of the pair of legs of the subject P, the one leg being estimated to be in the stance leg state, i.e. the one leg being highly likely to be the supporting leg when the subject P changes the position and attitude of the torso (refer to Table 2 and FIG. 4). Hence, when the reference point Q (m) is changed, the position of the current reference point Q (m) can be estimated with high accuracy on the basis of the position of the previous reference point Q (m−1) before the change and according to the attitudes of the torso and the one leg at the time point at which the current reference point is defined after the change (refer to FIG. 5).

As a result, based on the current reference point position Q (m), the specified point position P (k (m)) and the temporal changes thereof can be estimated with high accuracy as the walking state of the subject according to the attitudes of the torso and the one leg after the time point at which the current reference point Q (m) is defined. The walking state may include the positions of the hip joint, the knee joints, and the foot joints.

Another Embodiment of the Present Invention

The tilt sensors S2 may be provided on at least a head, arms or the like in addition to the pair of legs and the torso, and the specified point positions P (k (m)), which are fixed to and defined at the head, the arms or the like, and the temporal changes thereof may be estimated as the walking state of the subject on the basis of the output signals of the tilt sensors S2.

What is claimed is:
1. A walking state estimating device comprising:
a first arithmetic processing element configured to distinguish, based on an output signal of a first sensor and as an actual state of a subject, on each of a pair of legs of the subject, between a stance leg state in which a bottom end portion is in contact with a floor surface and a swing leg state in which the bottom end portion is off the floor surface, and to define, provided that one leg of the pair of legs has been distinguished as being in the stance leg state, a reference point at the bottom end portion of the one leg;

a second arithmetic processing element configured to measure attitudes of a torso and the pair of legs of the subject based on an output signal of a second sensor; and a third arithmetic processing element configured to estimate, in the case where the first arithmetic processing element has defined a current reference point, based on the output signal of the first sensor, that is different from a previous reference point, the position of the current reference point on the basis of the position of the previous reference point and the attitudes of the torso and the pair of legs of the subject measured by the second arithmetic processing element, based on the output signal of the second sensor, at the time point of the definition of the current reference point, and to estimate the position of a specified point fixed to and defined at the torso on the basis of the position of the current reference point and the attitudes of the torso and one leg at which the current reference point has been defined, the attitudes having been measured by the second arithmetic processing element, based on the output signal of the second sensor, after the time point of the definition of the current reference point, wherein the first arithmetic processing element, the second arithmetic processing element, and the third arithmetic processing element are constituted of the same processor or separate processors.

2. The walking state estimating device according to claim 1, wherein the third arithmetic processing element is configured to estimate, in the case where the first arithmetic processing element has estimated that both of the pair of legs are in the stance leg state, a difference in height between the bottom end portions of the pair of legs on the basis of the attitudes of the torso and the pair of legs of the subject measured by the second arithmetic processing element so as to estimate the shape of the floor surface on the basis of the difference in height or to correct the position of the current reference point on the basis of the difference in height.

3. The walking state estimating device according to claim 2, wherein the third arithmetic processing element is configured to determine whether the difference in height is a threshold value or less and output an estimation result indicating that the floor surface is a level surface in the case where a result of the determination is affirmative.

4. The walking state estimating device according to claim 3, wherein the third arithmetic processing element is configured to determine whether the difference in height is the threshold value or less by using the threshold value set on the basis of an occurrence frequency distribution of the difference in height obtained from the results of a plurality of times of estimations of the difference in height or by using the threshold value set beforehand on the basis of an error of measurement by the second arithmetic processing element.

5. The walking state estimating device according to claim 1, wherein the first arithmetic processing element is configured to estimate that the other leg is in the stance leg state in the case where it is estimated that one leg of the pair legs at which the previous reference point has been defined at the bottom end portion thereof has been changed from the stance leg state to the swing leg state.

6. A walking state estimating method comprising:

a first arithmetic processing step configured to distinguish, based on an output signal of a first sensor and as an actual state of a subject, on each of a pair of legs of the subject, between a stance leg state in which a bottom end portion is in contact with a floor surface and a swing leg state in which the bottom end portion is off the floor surface, and to define, provided that one leg of the pair of legs has been distinguished as being in the stance leg state, a reference point at the bottom end portion of the one leg;

a second arithmetic processing step configured to measure attitudes of a torso and the pair of legs of the subject based on an output signal of a second sensor; and a third arithmetic processing step configured to estimate, in the case where a current reference point, defined based on the output signal of the first sensor, that is different from a previous reference point has been defined in the first arithmetic processing step, the position of the current reference point on the basis of the position of the previous reference point and the attitudes of the torso and the pair of legs of the subject measured in the second arithmetic processing step, based on the output signal of the second signal, at the time point of the definition of the current reference point, and to estimate the position of a specified point fixed to and defined at the torso on the basis of the position of the current reference point and the attitudes of the torso and one leg at which the current reference point has been defined, the attitudes having been measured in the second arithmetic processing step, based on the output signal of the second sensor, after the time point of the definition of the current reference point.

* * * * *